United States Patent [19]

Vlattas

[11] Patent Number: 4,477,379
[45] Date of Patent: Oct. 16, 1984

[54] IMIDAZOBENZOTHIADIAZEPINES

[75] Inventor: Isidoros Vlattas, Summit, N.J.

[73] Assignee: Ciba-Geigy Corporation, Ardsley, N.Y.

[21] Appl. No.: 406,759

[22] Filed: Aug. 9, 1982

Related U.S. Application Data

[60] Division of Ser. No. 259,261, May 11, 1981, Pat. No. 4,391,808, which is a continuation-in-part of Ser. No. 158,671, Jun. 12, 1980, abandoned.

[51] Int. Cl.³ ............................................ C07D 513/04
[52] U.S. Cl. ................................................. 260/243.3
[58] Field of Search ..................................... 260/243.3

*Primary Examiner*—Glennon H. Hollrah
*Assistant Examiner*—D. B. Springer
*Attorney, Agent, or Firm*—Norbert Gruenfeld

[57] ABSTRACT

5-Diazacycloalkyl-imidazo[imidazo]2,1-b][1,3,5]benzothiadiazepines of the formula

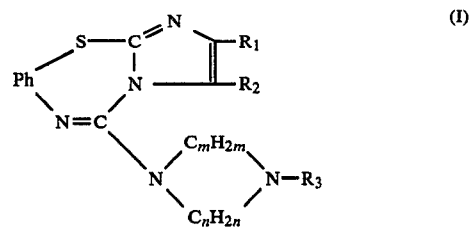

e.g. a compound of formula I wherein Ph=phenylene, $m=2$, $n=3$, $R_1$ and $R_2=H$, and $R_3=$methyl, oxides and salts thereof, are neuroleptic agents.

3 Claims, No Drawings

IMIDAZOBENZOTHIADIAZEPINES

CROSS REFERENCE TO RELATED APPLICATION

This is a divisional application of application Ser. No. 259,261, now U.S. Pat. No. 4,391,808, which is a continuation-in-part of application Ser. No. 158,671 filed June 12, 1980, now abandoned.

SUMMARY OF THE INVENTION

The present invention concerns and has for its object the provision of new 5-diazacycloalkyl-imidazo [2,1-b][1,3,5]-benzothiadiazepines, more particularly of those corresponding to Formula I

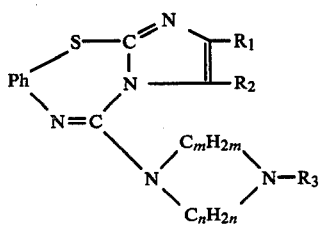

wherein each of $R_1$ and $R_2$ is hydrogen, lower alkyl or lower alkanoyl, halogeno, cyano, carboxy, lower carbalkoxy, carbamoyl, sulfamoyl, mono- or di-lower alkyl-(carbamoyl or sulfamoyl); Ph is 1,2-phenylene, unsubstituted or substituted by up to two members selected from lower alkyl, lower alkoxy, lower alkylthio, halogeno, trifluoromethyl, sulfamoyl, mono- or di-lower alkysulfamoyl; each of $C_mH_{2m}$ and $C_nH_{2n}$ is lower alkylene separating both nitrogen atoms by 2 or 3 carbon atoms, and $R_6$ is hydrogen, lower alkyl, alkanoyl, alkoxycarbonyl, phenylalkoxycarbonyl, or hydroxyalkyl, wherein the hydroxy group is separated from the nitrogen atom by at least 2 carbon atoms; their N- and/or S-oxides, lower alkylquaternaries and salts thereof, derived from pharmaceutically acceptable acids or bases; as well as of corresponding pharmaceutical compositions and of methods for the preparation and application of said products, which are useful neuroleptic agents lacking extrapyramidal side-effects, which are suitable, for example, in the treatment or management of aggression, agitation and/or anxiety in mammals.

DESCRIPTION OF THE PREFERRED EMBODIMENTS

A lower alkyl group $R_1$, $R_2$, $R_3$ and/or such present in a substituted 1,2-phenylene Ph-group, as well as in said alkoxy, alkylthio or said other alkylated groups, is above all methyl, but also ethyl, n- or i-(propyl, butyl, pentyl, hexyl or heptyl), e.g. 2-methylpropyl or 3-methylbutyl; and alkanoyl is preferably acetyl or propionyl.

A halogen atom $R_1$ and/or $R_2$, or such present in Ph, is preferably fluoro or chloro, but also bromo.

A lower carbalkoxy, mono- or dialkylcarbamoyl or -sulfamoyl group $R_1$ and/or $R_2$, or present in Ph, is preferably carbomethoxy, carbethoxy; mono- or dimethylcarbamoyl or -sulfamoyl respectively.

A 1,2-phenylene radical Ph is preferably unsubstituted, or mono-substituted in the benzene ring by said substituents, for example methyl or ethyl; methoxy, ethoxy or i-propoxy; methylthio or ethylthio; fluoro, chloro or bromo; trifluoromethyl; sulfamoyl, mono- or dimethylsulfamoyl.

A lower alkylene group $C_mH_{2m}$ and $C_nH_{2n}$ is especially ethylene; but also 1,2- or 1,3-propylene, 1,2-, 1,3- or 2,3-butylene; thus forming with both adjacent nitrogen atoms preferably a piperazino or homopiperazino moiety.

A lower alkoxycarbonyl or hydroxyalkyl group $R_3$ is preferably methoxycarbonyl or ethoxycarbonyl; 2-hydroxy-(ethyl or propyl), 3-hydroxy-(propyl or butyl) or 4-hydroxybutyl respectively.

Said N-oxides are preferably those in which $R_3$ is lower alkyl or hydroxyalkyl, and in which the oxygen is attached to the nitrogen carrying said $R_3$ group. Said S-oxides represent sulfoxides(SO) or sulfones ($SO_2$).

Similarly, said lower alkylquaternaries of the compounds of Formula I are preferably derived from those wherein $R_3$ is lower alkyl or hydroxyalkyl, and wherein only the terminal piperazino or homopiperazino-nitrogen atom is quaternized. The anions of said quaternaries, as well as those of said acid addition salts, are preferably those of pharmaceutically acceptable acids, e.g. those listed below. Those compounds of Formula I with $R_1$ and/or $R_2$ being carboxy, also form salts with such bases, e.g. ammonia, mono-, dl- or tri-lower alkylamines; lower alkyleneimines; morpholine, piperazine, pyridine or lower alkyl-derivatives of said cyclic bases; alkali metal or alkaline earth metal hydroxides.

The term "lower," referred to above or hereinafter in connection with organic radicals or compounds respectively, defines such with up to 7, preferably up to 4, and advantageously those with one or two carbon atoms.

The compounds of the invention exhibit valuable pharmacological properties, primarily neuroleptic activity. It is demonstrable in animal tests using advantageously mammals, e.g. mice, rats or monkeys, as test objects. Said compounds can be administered to them enterally or parenterally, advantageously orally, or subcutaneously, intravenously or intraperitoneally, for example, within gelatin capsules, or in the form of starchy suspensions or aqueous solutions respectively. The applied dosage may range between about 0.01 and 100 mg/kg/day, preferably between about 0.05 and 10 mg/kg/day, advantageously between about 0.1 and 5 mg/kg/day.

Said neuroleptic properties can be demonstrated in adult rats or squirrel monkeys, which were trained to press a lever to avoid the onset of an electric foot shock. Each lever press postpones the shock for 30 seconds. Whenever the animal fails to press the lever once within said period, brief (0.5 sec.) shocks are delivered at 15 second intervals until the animal again presses the lever. Under control conditions the animals press the lever at a moderately steady rate and seldom receive more than five or six shocks during a 25-minute (rats) and up to 4-hour experimental session. Said compounds, which are administered to the animals 30, 90 and 210 minutes prior to the experimental session, block the learned conditioned avoidance behavior, manifested by a decrease in avoidance responding and a marked increase in shocks taken by the animals. Both, the avoidance responses and failures (shocks received), are recorded separately for evaluation according to said Sidman Avoidance test. Compounds of the invention decrease avoidance responses, e.g. compound of example 1 decreases avoidance responses in rats and monkeys at an oral dose of 10 mg/kg or lower.

The extrapyramidal side-effects (EPS) known from classical neuroleptics, have been found to induce a characteristic motor syndrome in squirrel monkeys, which were previously exposed to repeated antipsychotic treatment. These movement disorders consist of dystonic postures and dyskinetic movements, and correlate much better with the reported incidence of EPS in man, than does catalepsy or tremor in this monkey. Thus, the potential extrapyramidal liability, as well as the relative incidence of other neurological signs, such as ptosis, can be assessed by observation of these adult male squirrel monkeys, weighing 700-1200 g. They are treated with haloperidol (1.25 mg/kg) once weekly or biweekly. After approximately 2-4 months of this treatment regimen, dystonic posture and dyskinetic movements are evident during 1-6 hours after administration of haloperidol. At no other time abnormal movements are evident in these monkeys. After haloperidol-elicited dyskinesias had developed, this regimen ends, and 1.25 mg/kg haloperidol is given once every 4-8 weeks as a control for comparison with test agents of this invention.

Said monkeys are individually observed at intervals of 2, 4 and 6 hours after treatment and the experiments are performed in an enclosed cubicle, which is equipped with a remotely controlled video observation system and a white noise generator. Observations are performed by two independent observers, neither of whom has prior knowledge of the agent administered, nor the purpose of the experiment. A third person handles the monkeys during neurological examination. After initial observations through the video system, the observers enter the cubicle, recording the monkeys' responses as "motor" (ambulation inside cage), "visual" (visual response but no ambulation) and "none" (no response). Activity, posture, tremors, salivation and other neurological signs are observed. Particular attention is devoted to the presence or absence of "bizarre", dystonic postures and dyskinetic movements, as previously characterized. The handler then removes the monkey from the cage and the monkey's reactions are separately scored to the approach of the gloved hand, to the initial touch during capture and to restraint after capture. Vocalization during capture is also recorded. The handler then evaluates body tone and pupil size, and scores the presence or absence of ptosis. Catalepsy is then assessed, if preliminary examination suggested that this sign might be present. The monkey is first positioned on the floor with his head down, then at the entrance to the observation cage, and finally inside the observation cage. If the monkey remains essentially immobile in any of these positions for at least 5 seconds, catalepsy is judged to be present. After the monkey re-enters, or is replaced inside its observation cage, it is again observed for at least 1 minute for dyskinesias. A given sign or rating, which differs from control, is only considered an agent-induced effect, if both observers recorded it during any of the three observation periods. When one observer considered a given sign to be of lesser magnitude than did the other observer, the less severe score is accepted. However, overall inter-observer correspondence is good.

After administration of 10 mg/kg of the illustrative compound of Example 1, only one of five monkeys showed any type of dyskinetic movement, and that was confined to one form (writhing) only, as observed during one of three time periods. In contrast, severe dyskinesia, characterized by various types of dyskinetic movements, is recognized in all monkeys treated with haloperidol (1.25 mg/kg). Dyskinesias were also absent after clozapine (10 mg/kg), but were apparent after a moderate dose of haloperidol (0.625 mg/kg) in five monkeys, and no dyskinesias were observed at any time after vehicle (excipient) treatment. However, clozapine produced hypersalivation in every monkey which was examined in this experiment, but no hypersalivation was apparent after any other treatment, including said Example 1 compound. Ptosis, catalepsy, reduction in body tone and reduced responses to the observers were noted in some or all monkeys after administration of said 3 illustrative agents.

According to said, and other classical tests, the compounds of the invention are useful neuroleptic (antipsychotic) agents, for example, in the treatment or management of aggression, agitation or anxiety, and are virtually devoid of extrapyramidal side-effects, as is clozapine in man. The absence of hypersalivation indicates advantages of said new compounds over clozapine, however. They are also useful intermediates in the preparation of other valuable products, especially of pharmacologically active compositions.

Particularly useful for their neuroleptic properties are compounds of Formula I, in which each of $R_1$ and $R_2$ is hydrogen, lower alkyl or alkanoyl, halogeno, cyano, carboxy, lower carbalkoxy, carbamoyl, sulfamoyl, mono- or di-lower alkyl-(carbamoyl or sulfamoyl); Ph is 1,2-phenylene, (lower alkyl)-1,2-phenylene, (lower alkoxy)-1,2-phenylene, (lower alkylthio)-1,2-phenylene, (halogeno)-1,2-phenylene, (trifluoromethyl)-1,2-phenylene, (sulfamoyl)1,2-phenylene, (mono- or di-lower alkylsulfamoyl)-1,2-phenylene; each of m and n is the integer 2 or 3; and $R_3$ is hydrogen, lower alkyl, alkanoyl, alkoxycarbonyl phenylalkoxycarbonyl, or hydroxyalkyl, wherein the hydroxy group is separated from the nitrogen atom by at least 2 carbon atoms; their N- and/or S-oxides; lower alkylquaternaries; or a pharmaceutically acceptable acid addition salt thereof.

Outstanding compounds of the invention are those of Formula II

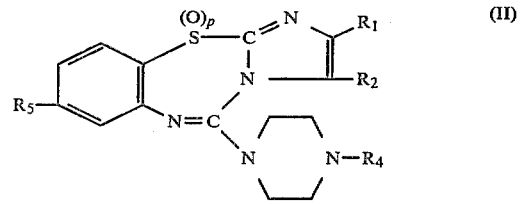

wherein each of $R_1$ and $R_2$ is hydrogen or lower alkyl; $R_4$ is hydrogen, lower alkyl or lower 2- or 3-hydroxyalkyl; $R_5$ is hydrogen, lower alkyl, lower alkoxy, halogeno or trifluoromethyl; and p is an integer from 0 to 2; the N-oxide thereof; or pharmaceutically acceptable acid addition salts thereof.

Preferred are those compounds of Formula II, wherein each of $R_1$ and $R_2$ is hydrogen or methyl; $R_4$ is alkyl or 2- or 3-hydroxyalkyl with up to 4 carbon atoms; $R_5$ is hydrogen, methyl, methoxy, fluoro, chloro or trifluoromethyl; and p is 0; the N-oxide thereof; or pharmaceutically acceptable acid addition salts thereof.

The compounds of the invention are prepared according to methods known per se, advantageously by condensing compounds of Formulae III and IV

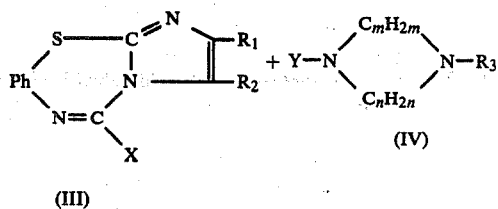

(III)

(IV)

wherein X is halogeno, lower alkoxy, lower alkylthio, cyanato or thiocyanato; Y is hydrogen or an alkali metal; and the remaining symbols have the meaning given for Formula I and, if desired, converting any resulting compound into another compound of Formula I.

Said condensation is advantageously carried our with an excess of the piperazine IV (Y=H), or with equivalent amounts of said metal derivatives thereof, preferably when X is halogeno, lower alkylthio or thiocyanato, advantageously at temperatures between about 0° and 150°, and preferably in an appropriate solvent such as a lower alkanol, for example amyl alcohol, dimethylformamide, hexamethylphosphoramide, toluene.

Another process for preparing the compounds of Formula I consists in ring-closing the compounds of Formula V

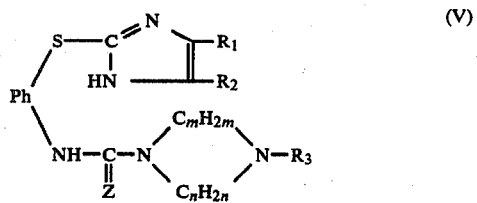

(V)

wherein Z is oxygen, sulfur, or NH, and the other symbols have the above-given meaning, under dehydrating, dehydrosulfurating conditions.

Said ring-closing conditions are achieved with strong dehydrating or dehydrosulfurating agents, such as phosphorous halides and/or oxyhalides, or cyanogen halides, with or without crown ether catalysts, such as 8-crown-6-ether, and with or without basic catalysts such as triethylamine or potassium carbonate, preferably in an inert solvent, such as dimethylformamide.

The novel starting imidazo[2,1-b][1,3,5]benzothiadiazepines of formula III are prepared according to ring closure methods known per se, advantageously by condensing compounds of formula VI wherein Ph, $R_1$ and $R_2$ have meaning given for compounds of formula III,

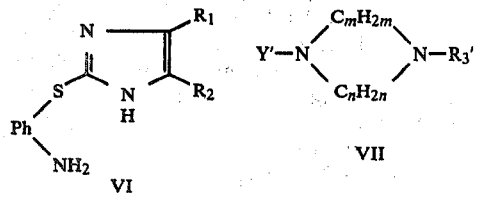

VI  VII with reactive carbonic acid derivatives such as phosgene, thiophosgene, 1,1'-carbonyldiimidazole, cyanogen bromide or the like.

Compounds of formula III wherein X is hydroxy can in turn be converted to compounds wherein X is sulfhydryl by conventional sulfurating agents, such as phosphorus pentasulfide, and these can be further derivatized to compounds of formula wherein X is as defined above analogous to the procedures illustrated by the examples herein.

The starting materials of Formula V can be obtained from that of the (tautomeric) precursors of Formula III, wherein X is hydroxy, thio or amino by condensing them with compounds of Formula IV in the presence or absence of other bases, e.g. those listed above, preferably in an inert solvent, such as methylene chloride or toluene at temperatures between 0° and 150° advantageously between 10° and 50°. The ring opening reaction is preferably carried out at low temperature to minimize side reactions when $R_1'$ and $R_2'$ represent reactive functional groups.

Alternately, starting materials of formula V, wherein $R_3$ is alkanoyl, alkoxycarbonyl or phenylalkoxycarbonyl, are prepared by condensing a compound of formula VI with a compound of formula VII wherein $Y^1$, represents halocarbonyl, halothiocarbonyl or cyano, and $R_3'$ represents alkanoyl, alkoxycarbonyl or phenylalkoxycarbonyl, preferably in an inert solvent, at temperatures between 0° and 150°.

The compounds of the invention so obtained can be converted into other compounds of Formula I according to known methods. Thus, for example, those with $R_3$ being hydrogen or alkali metal, e.g., sodium or lithium salts thereof, can be reacted with substituted or unsubstituted oxiranes, such as ethylene oxide, or reactive esters of unsubstituted or correspondingly substituted aliphatic or araliphatic alcohols such as methanol, ethanol, allyl alcohol, propargyl alcohol, e.g. such esterified by a strong inorganic or organic acid, above all hydrohalic acids, e.g. hydrochloric, hydrobromic or hydriodic acid; sulfuric or an aromatic sulfonic acid, e.g. p-toluene or m-bromobenzene sulfonic acid, in order to obtain the corresponding N-substituted compounds or quaternaries respectively, depending on the molar amount of the alkylating agent employed. Intermediates of formula I wherein $R_3$ is alkali metal are obtained by metallation with reactive organo metallic agents such as lithium diisopropylamide, with alkali metal alkoxides such as sodium methoxide, or alkali metal hydrides such as sodium or potassium hydride.

Unsaturated compounds, such as those with $R_3$ being lower alkenyl, lower alkynyl may be hydrogenated with catalytically activated hydrogen to obtain compounds wherein $R_3$ is the corresponding lower alkyl. Conversely, resulting N-alkylated compounds can be converted into N-unsubstituted compounds, e.g. by catalytic hydrogenolysis of N-benzyl compounds, or reaction of N-lower alkyl derivatives with lower alkyl haloformates, e.g. ethyl chloroformate, to yield N-acyl derivatives which, in turn, may be hydrolyzed to said unsubstituted compounds, those with $R_3$=H, for example with aqueous bases, such as alkali metal hydroxides, such as aqueous sodium hydroxide solution.

Compounds of formula I wherein $R_3$ is hydroxyalkyl can also be prepared by first reacting corresponding compounds of Formula I, wherein $R_3$ represents hydrogen, with reactive derivatives of corresponding glycols, glycolic acids or dicarboxylic acids, such as lower alkyl esters, halides or anhydrides thereof, or reactive esters of said glycols or glycolic acids derivatives, for example with hydrohalic or aromatic sulfonic acids, 1,2-dibromoethane or -propane, ethyl bromoacetate or -propionate, ethyl tosyloxyacetate; diethyl oxalate or malonate or ethyl oxalyl chloride. The intermediates so obtained are either hydrolyzed or reduced with simple or complex light metal hydrides such as lithium aluminum hydride, alone or with diborane to compounds of formula I wherein $R_3$ is hydroxyalkyl.

Compounds of formula I wherein $R_3$ is methyl can be prepared by reacting the corresponding compounds of formula I wherein $R_3$ represents hydrogen with lower alkyl- or phenyl lower alkyl- haloformates, such as ethyl chloroformate, to obtain compounds of formula I wherein $R_3$ is alkoxycarbonyl or phenylalkyloxy-carbonyl, and reducing said acyl derivatives with simple or complex light metal hydrides such as lithium aluminum hydride, sodium tri-t-butoxy or bis-(2-methoxyethoxy) aluminum hydride.

N-Acylated derivatives can be obtained from compounds of Formula I with $R_3$ being hydrogen, and corresponding reactive acid derivatives, e.g., halides, simple or activated esters, such alkyl or cyanoalkyl esters, anhydrides or isocyanates. Resulting compounds of Formula I with $R_1$ and/or $R_2$ being hydrogen, can be converted to the corresponding 3- and/or 4-(halo or acyl)-derivatives, e.g. by halogenation, preferably with chlorine in acetic acid or under Friedel-Crafts-conditions, and/or by acylation with a trihaloacetyl halide or a halosulfonic acid, followed by treatment with an alkali metal lower alkoxide, hydroxide or amide. Resulting carboxylic or sulfonic acid derivatives may then be hydrolyzed in known fashion, preferably under alkaline conditions and/or amidized with ammonia, mono- or di-lower alkylamines, and resulting carboxyamides may be dehydrated to the corresponding nitriles according to conventional methods.

Resulting tertiary nitrogen compounds with $R_3$ different from hydrogen, can be converted into the N- and/or S-oxides, for example with hydrogen peroxide or organic peracids, such as lower peralkanoic or perbenzoic acids, e.g. peracetic or m-chloro-perbenzoic acid, advantageously at temperatures at or below room temperature with the latter, or up to 100° with diluted hydrogen peroxide in the presence of lower alkanoic acids, e.g. acetic acid. If only N-oxides are desired, care should be taken, especially with said peracids, in order to prevent S-oxidation at overly long reaction times.

If only S-oxides are desired, compounds wherein $R_3$ is acyl, such as alkoxycarbonyl or phenylalkoxycarbonyl, are treated with hydrogen peroxide or organic peracids, preferably m-chloro-perbenzoic acid advantageously at temperatures at or below room temperature to obtain either sulfoxides (SO) or sulfones ($SO_2$) depending on the quantity of peracid used. Resulting compounds with $R_3$ being phenylalkoxy carbonyl or alkoxycarbonyl so obtained can be converted to other compounds of formula I according to methods known per se and previously described above.

Finally, the compounds of the invention are either obtained in the free basic form, or as a salt thereof. Any resulting base can be converted into a corresponding acid addition salt preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. Said acid addition salts are such of pharmaceutically acceptable inorganic or organic acids, such as strong metalloidic acids, for example hydrohalic, e.g. hydrochloric or hydrobromic acid; sulfuric, phosphoric, nitric or perchloric acid; but preferably such of aliphatic or aromatic carboxylic or sulfonic acids, e.g. formic, acetic, propionic, succinic, glycollic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, toluenesulfonic, naphthalenesulfonic, sulfanilic or cyclohexylsulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

In case mixtures of geometrical or optical isomers of the above compounds, e.g. I to VII are obtained, these can be separated into the single isomers by methods in themselves known, e.g. by fractional distillation, crystallization and/or chromatography. Racemic products can likewise be resolved into the antipodes, for example, by separation of diastereomeric salts thereof, e.g. by the fractional crystallization of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g. those of Formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 Kg weight may contain between about 5 and 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

To the mixture of 501 g of 1-methylpiperazine and 6,000 ml of amyl alcohol, 538 ml of 9.3N methanolic hydrogen chloride are added and the mixture is stirred and distilled for 1 hour, during which time 1,000 ml of distillate is collected and the temperature reaches 131°. Thereupon another 501 g of 1-methylpiperazine are added, followed by 618.5 g of 5-methylthio-imidazo[2,1-b][1,3,5]benzothiadiazepine. The mixture is stirred under nitrogen at 132°-140° for 48 hours and evaporated at about 80°-90°. The residue is dissolved in 3,000 ml of methylene chloride, the solution washed 3 times with 1,000 ml of 3N aqueous sodium hydroxide and 5 times with 1,000 ml of water. It is finally extracted 4 times with 750 ml of 2N hydrochloric acid each, the combined extracts are washed once with 1,000 ml of methylene chloride, decolorized with 75 g of charcoal, filtered and the filtrate is basified with 500 ml of 29.9% aqueous ammonia to a pH of 9-10. The mixture is extracted twice with 2,000 ml of methylene chloride, the combined extracts dried, filtered and evaporated at about 60°. 2,810 g of this residue are dissolved in 14,000 ml of hot isopropanol, the solution treated with 563 g of charcoal, filtered and the residue washed with 1,000 ml of cold isopropanol. The combined filtrates are reheated and again treated with 563 g of charcoal in the same manner. The resulting clear solution is concentrated to 8,500 ml and the concentrate allowed to stand in the refrigerator for 2 days. The white precipitate is filtered off, washed 3 times with cold isopropanol and dried at 40°/5 mmHg, to yield the 5-(4-methyl-piperazino)-imidazo[2,1-b][1,3,5]benzothiadiazepine of the formula

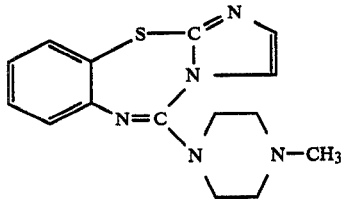

melting at 145°-147°.

1,614 g thereof are dissolved in 5,450 ml of anhydrous ethanol at 50°-60°, the solution filtered hot, the filter rinsed with 1,000 ml more anhydrous ethanol and the combined filtrates are acidified with the solution of 688 g of maleic acid in 1,600 ml of anhydrous ethanol while stirring. The mixture is stirred while cooling to 25°, the precipitate collected, washed twice with 800 ml of anhydrous ethanol and dried at 75°/0.5 mm Hg, to yield the corresponding monomaleate melting at 198°-199° with decomposition.

The starting material is prepared as follows: To 39,230 ml of 2N hydrochloric acid, 7,500 g of aminoacetaldehyde dimethylacetal are added during 45 minutes while stirring under nitrogen, followed by 6,932 g of potassium thiocyanate, which are added all at once. The mixture is heated to 98°, stirred for 2 hours and allowed to cool to room temperature overnight. The resulting suspension is stirred and cooled to 5°, filtered and the residue dried at 60°/5 mmHg, to yield the imidazole-2-thiol melting at 224°-226°.

2,468 g thereof are added to the solution of 1,604 g of 86.9% aqueous potassium hydroxide in 24,700 ml of isopropanol while stirring under nitrogen at room temperature, followed by 4,986 g of 2-bromo-nitrobenzene. The mixture is stirred and heated to 82°-85° for 5 hours, cooled to 50° and diluted with 37,000 ml of water. The resulting suspension is stirred at room temperature for 2 days, filtered, the residue washed 6 times with 4,000 ml of water and 5 times with 3,700 ml of diethyl ether, and dried at 60°/5 mmHg, to yield the 2-(o-nitrophenylthio)-imidazole melting at 178°-180°.

The mixture of 2,210 g thereof, 2,000 ml of water, 2,000 ml of ethanol and 1,700 g of iron powder is heated to 70° while stirring under nitrogen. After addition of 10 ml of concentrated hydrochloric acid the mixture is refluxed for 1.5 hours, whereupon 200 ml of concentrated hydrochloric acid in 1,000 ml of ethanol are added during 95 minutes. The mixture is refluxed for 2 hours longer and 400 ml of 6N aqueous sodium hydroxide are added. The resulting suspension is diluted with 2,000 ml of methanol, filtered and the residue is washed 3 times with 1,000 ml of methanol. The combined filtrates are diluted with 40,000 ml of water, the resulting suspension allowed to settle overnight, the precipitate is collected, washed twice with 2,000 ml of water and dried at 60°/5 mmHg, to yield the 2-(o-aminophenylthio)-imidazole melting at 137°-138°.

4,775 g thereof are added to the mixture of 55,000 ml of methylene chloride and 6,975 ml of triethylamine, the mixture cooled to 3° and 3,301 g of 85% thiophosgene in carbon tetrachloride are added during 2.5 hours while stirring under nitrogen at 15°. Stirring is continued at 10° for 4 hours and at room temperature overnight. The resulting suspension is filtered, the residue washed twice with 4,000 ml of methylene chloride and once with 20,000 ml of water and suspended in 11,000 ml of 1.3N hydrochloric acid. The suspension is stirred for 2 hours, filtered, the residue washed 3 times with 4,000 ml of water and dried at 60°/5 mmHg, to yield the imidazo[2,1-b][1,3,5]benzothiadiazepin-5(6H)-thione melting at 156°-159°.

1,184 g thereof are added to the solution of 278 g of sodium methoxide in 22,500 ml of isopropanol and the mixture is stirred for 1.5 hours under nitrogen. Thereupon 791 g of methyl iodide are added during 30 minutes and the mixture is stirred 3.5 hours longer at about 20°. It is diluted with 45,000 ml of water and the resulting suspension stirred at room temperature overnight. It is filtered, the residue washed 5 times with 4,000 ml of water and dried at 60°/5 mmHg, to yield the 5-methylthio-imidazo[2,1-b][1,3,5]benzothiadiazepine melting at 116°-118°.

Similarly the following starting materials are prepared from the correspondingly substituted 2-bromonitrobenzenes:
  a. 8-methoxy-5-methylthio-imidazo[2,1-b][1,3,5]benzothiadiazepine, melting at 143°–146°;
  b. 8-chloro-5-methylthio-imidazo[2,1-b][1,3,5]benzothiadiazepine melting at 147°–149°;
  c. 8-fluoro-5-methylthio-imidazo[2,1-b][1,3,5]benzothiadiazepine melting at 174°–176°;
  d. 8-methyl-5-methylthio-imidazo[2,1-b][1,3,5]benzothiadiazepine

EXAMPLE 2

To the solution of 480 mg of 5-thiocyanatoimidazo[2,1-b][1,3,5]benzothiadiazepine in 1 ml of hexamethylphosphoramide, 500 mg of 1-methylpiperazine are added during 5 minutes while stirring under nitrogen at −5°. Stirring is continued for 5 minutes at said temperature, and for 15 minutes at room temperature. The mixture is diluted with 80 ml of ethyl acetate, washed twice with saturated aqueous sodium chloride, dried and evaporated. The residue is dissolved in 2 ml of acetone, the solution acidified with 300 mg of maleic acid and diluted with diethyl ether, to yield the 5-(methylpiperazino)-imidazo[2,1-b][1,3,5]benzothiadiazepine monomaleate, melting at 198°–199° with decomposition; it is identical with that of Example 1.

The starting material is prepared as follows: To the suspension of 1.44 g of 50% sodium hydride in mineral oil and 150 ml of dry tetrahydrofuran, 6.45 g of imidazo[2,1-b][1,3,5]benzothiadiazepin-5(6H)-thione are added in portions, and the mixture is stirred at room temperature under nitrogen for one hour. The resulting white suspension is cooled to 0° and the solution of 3.5 g of cyanogen bromide in 10 ml of tetrahydrofuran are added dropwise. The mixture is stirred at room temperature for 0.5 hour and evaporated. The residue is triturated with methylene chloride, the mixture washed with water, dried, concentrated to a small volume, washed with diethyl ether and filtered, to yield the 5-thiocyanatoimidazo[2,1-b][1,3,5]benzothiadiazepine melting at 111°–113°.

EXAMPLE 3

The mixture of 333 mg of 1-[2-(imidazo-2-ylthio)-phenyliminothiocarbonyl]-4-methylpiperazine, 3.3 ml of dimethylformamide, 276 mg of potassium carbonate, 116 mg of cyanogen bromide and 50 mg of 8-crown-6 ether is stirred at room temperature under nitrogen for 3 hours. It is diluted with ethyl acetate, washed with saturated aqueous sodium chloride, dried and evaporated. The residue is dissolved in acetone, the solution treated with 116 mg of maleic acid and diluted with diethyl ether, to yield the 5-(4-methylpiperazino)-imidazo[2,1-b][1,3,5]benzothiadiazepine monomaleate, melting at 198°–199° with decomposition; it is identical with that of Example 1.

The starting material is prepared as follows: The mixture of 2.3 g of imidazo[2,1-b][1,3,5]benzothiadiazepin-5(6H)-thione, 23 ml of methylene chloride and 1.0 g of 1-methylpiperazine is stirred at room temperature for 15 hours. The crystalline product formed is filtered off and washed with methylene chloride, to yield the 1-[2-(imidazo-2-ylthio)-phenyliminothiocarbonyl]-4-methylpiperazine melting at 209°–212°.

EXAMPLE 4

To the suspension of 3.1 g of 1-[2-(imidazo-2-ylthio)-phenyliminocarbonyl]-4-methylpiperazine and 25 ml of phosphorus oxychloride, 2.04 g of phosphorus pentachloride are added at once, and the mixture is stirred at room temperature for 4 hours. It is evaporated, the residue suspended in 50 ml of dry methylene chloride, the suspension cooled to 0° and 2.02 g of triethylamine are added dropwise while stirring. Stirring is continued for 15 minutes at 0°, the mixture washed with water, dried and evaporated. The residue is dissolved in acetone, and the solution acidified with maleic acid, to yield the 5-(4-methylpiperazino)-imidazo[2,1-b][1,3,5]benzothiadiazepine monomaleate, melting at 198°–199° with decomposition; it is identical with that of Example 1.

The starting material is prepared as follows: The mixture of 15 g of 2-(imidazo-2-ylthio)-aniline, 13.9 g of 1,1'-carbonyldiimidazole and 675 ml of methylene chloride is stirred at room temperature for 24 hours. The solids formed are filtered off and washed with methylene chloride to yield the imidazo[2,1-b][1,3,5] benzothiadiazepin-5-(6H)-one, melting at 250°–252° with decomposition.

In the analogous manner (or by replacing the 1,1'-carbonyldiimidazole by the equivalent amount of phosgene), the following intermediates are obtained and are illustrative of the process:
  a. 3,4-dimethylimidazo[2,1-b][1,3,5]benzothiadiazepin-5(6H)-one, m.p. 225° (dec.);
  b. 8-chloroimidazo[2,1-b][1,3,5]benzothiadiazepin-5(6H)-one, m.p. 261°–263°;
  c. 8-trifluoromethylimidazo[2,1-b][1,3,5]benzothiadiazepin-5(6H)-one, m.p. 257°–260°.
  d. 3-methylimidazo[2,1-b][1,3,5]benzothiadiazepin-5(6H)-one, m.p. 225°–229°.

The mixture is 2.17 g of imidazo[2,1-b][1,3,5]benzothiadizepin-5(6H) 1.0 g of 1-methyl piperazine and 20 ml of methylene chloride is stirred at room temperature for 24 hours. The crystalline product formed is filtered off and washed with methylene chloride, to yield the 1-[2-(imidazo-2-ylthio)-phenyliminocarbonyl]-4-methylpiperazine, melting at 197°–200°.

In similar manner the following additional starting materials are obtained and are illustrative of the process:
  a. 1-[2-(4-methylimidazo-2-ylthio)-phenyliminocarbonyl]-4-methylpiperazine melting at 101°–5° (dec.).
  b. 1-[2-(imidazo-2-ylthio)-phenyliminocarbonyl]-4-methylhomopiperazine, melting at 134°–138°.
  c. 1-[2-(imidazo-2-ylthio)-phenyliminocarbonyl]-4-carboethoxypiperazine, melting at 161°–170°.
  d. 1-[2-(imidazo-2-ylthio)-phenyliminocarbonyl]-4-carbobenzoxypiperazine, melting at 206°–208°.
  e. 1-[2-(4-carboethoxyimidazo-2-ylthio)-phenyliminocarbonyl]-4-methylpiperazine, melting at 166°–169°.
  f. 1-[2-(imidazo-2-ylthio)-4-trifluoromethylphenyl iminocarbonyl]-4-methylpiperazine melting at 212°–214° C.

EXAMPLE 5

A mixture of 10 g of 5-methylthio-imidazo[2,1-b][1,3,5]benzothiadiazepine hydrochloride, 3.62 g of piperazine, and 350 ml of amyl alcohol is refluxed with stirring and under nitrogen for 20 hrs. The solvent is evaporated under vacuum, the residue is triturated with methylene chloride, washed with 2N sodium hydroxide solution, dried over MgSO₄, and evaporated to dryness. The residue is dissolved in 10 ml of methanol and treated with 2N ethereal hydrochloric acid solution to give 5-(4H-piperazino)imidazo[2,1-b][1,3,5]benzothiadiazepine dihydrochloride, melting at 249° C. with decomposition.

EXAMPLE 6

A mixture of 5 g of 5-methylthio-imidazo[2,1-b][1,3,5]benzothiadiazepine hydrochloride, 2.86 g of N-β-hydroxyethylpiperazine, and 175 ml of amyl alcohol is refluxed under nitrogen for 48 hrs. with stirring. The solvent is removed under vacuum, the residue is triturated with methylene chloride, washed with 2N sodium hydroxide solution, dried over MgSO₄, and evaporated to dryness. The residue is dissolved in 5 ml of methanol and treated with 2N ethereal hydrochloric acid solutions to give 5-(4-β-hydroxyethylpiperazino)-imidazo[2,1-b][1,3,5]benzothiadiaz epine dihydrochloride melting at 212°–214°.

EXAMPLE 7

By replacement of the N-β-hydroxyethylpiperazine in example 6 by an equivalent amount of N-methyl-homopiperazine one obtains 5-(4-methyl-homopiperazino)imidazo[2,1-b][1,3,5]benzothiadiazepine, isolated as the fumarate salt melting at 216°–8°.

EXAMPLE 8

According to the methods illustrated by the previous examples, the following compounds of Formula I are obtained from equivalent amounts of the corresponding starting materials; Ph=4-R₅-1,2-phenylene; $C_mH_{2m}$=(CH₂)₂; $C_nH_{2n}$=(CH₂)$_{n'}$.

ethereal hydrochloric acid solution is added and the resulting precipitate is collected. Recrystallization from methanol-ethyl acetate yields 5-(4-methyl-4-oxidopiperazino)-imidazo[2,1-b][1,3,5]benzothiadiazepine hydrochloride, melting at 155° with decomposition.

EXAMPLE 11

(a) To the solution of 0.5 g of 5-(4-carbobenzoxypiperazino)-imidazo[2,1-b][1,3,5]benzothiadiazepine in 5 ml of methylene chloride, cooled at 0° C., is added dropwise a solution of 0.26 g of m-chloroperbenzoic acid dissolved in 2 ml of methylene chloride. The mixture is stirred at 0° C. for 1.5 hrs., the solids are filtered, and the filtrates are washed with 10% aqueous potassium carbonate and water, then dried over magnesium sulfate and evaporated to dryness to give 5-(4-carbobenzoxypiperazino)-imidazo[2,1-b][1,3,5]benzothiadiazepine 1-oxide.

Mass spec.: m/e 435, 418, 387.

(b) In a similar manner and by using 0.61 g (2 equivalents) of m-chloroperbenzoic acid, the 5-(4-carbobenzoxypiperazino)-imidazo[2,1-b][1,3,5]benzothiadiazepine 1,1-dioxide is obtained.

Mass spec.: m/e 451, 420, 406, 386.

EXAMPLE 12

(a) To the solution of 100 mg of 5-(4-carbobenzoxypiperazino)-imidazo[2,1-b][1,3,5]benzothiadiazepine 1-oxide in 0.3 ml of acetic acid are added 0.35 ml of a 2N solution of hydrobromic acid in acetic acid. The mixture is heated at 100° C. for 1 hr. and stirred at room temperature overnight. Ether is added, and the 5-(4H-piperazino)-imidazo[2,1-b][1,3,5,]benzothiadiazepine

| No. | R₁ | R₂ | R₃ | n' | R₅ | Salt | m.p. °C. |
|---|---|---|---|---|---|---|---|
| 1 | H | H | H | 2 | H | 2HCl | 249 dec. |
| 2 | H | H | CH₃ | 2 | H | 2HCl | 216–219 |
| 3 | H | H | CH₃ | 2 | OCH₃ | 2HCl | 155 dec. |
| 4 | H | H | CH₃ | 2 | F | maleate | 202–204 |
| 5 | H | H | CH₃ | 2 | Cl | 2HCl | 203–206 |
| 6 | H | H | CH₃ | 2 | CF₃ | 2HCl | 180 dec. |
| 7 | CO₂C₂H₅ | H | CH₃ | 2 | H | — | 138–141 |
| 8 | H | H | (CH₂)₂OH | 2 | H | 2HCl | 210–212 |
| 9 | H | H | COOEt | 2 | H | — | 137–139 |
| 10 | H | H | CH₃ | 3 | H | fumarate | 216–218 |
| 11 | H | H | COOCH₂C₆H₅ | 2 | H | — | NMR: 5.2, 3.5 |
| 12 | CH₃ | H | CH₃ | 2 | H | maleate | 191–192.5 |
| 13 | CH₃ | CH₃ | CH₃ | 2 | H | | |

EXAMPLE 9

To the solution of 0.2 g of 5-(4-carboethoxypiperazino)-imidazo[2,1-b][1,3,5]benzothiadiazepine in 2 ml of dry tetrahydrofuran, 100 mg of lithium aluminum hydride are added at once and the mixture is refluxed under nitrogen for 48 hrs. The mixture is cooled to room temperature, stirred with 0.2 ml of 30% sodium hydroxide, and filtered. The filtrates were evaporated to dryness and the product is purified to give 5-(4-methylpiperazino]-imidazo[2,1-b][1,3,5]benzothiadiazepine, melting at 145°–7°, and identical to compound obtained in example 1.

EXAMPLE 10

To the solution of 88 mg of 5-(4-methylpiperazino)-imidazo[2,1-b][1,3,5]benzothiadiazepine in 1 ml of methylene chloride, 74 mg of m-chloroperbenzoic acid are added at 0° C. The mixture is stirred at 0° C. overnight; this is diluted with 1 ml of ether, one equivalent of 1-oxide hydrobromide is filtered and washed with ether; m.p. 75° dec.

(b) In a similar manner the 5-(4-carbobenzoxypiperazino)-imidazo[2,1-b][1,3,5]benzothiadiazepine 1,1-dioxide is converted to 5-(piperazino)-imidazo[2,1-b][1,3,5]benzothiadiazepine 1,1-dioxide hydrobromide. Rf=0.353 (silica gel, ethyl acetate-methylene chloride, 1:1).

EXAMPLE 13

A mixture of 285 mg of 5-(4H-piperazino)-imidazo[2,1-b][1,3,5]benzothiadiazepine, 0.5 g of potassium carbonate, 0.142 g of methyl iodide and 2 ml of acetone is stirred at room temperature overnight and evaporated. Water is added to the residue, and the mixture is extracted with methylene chloride. The extracts are dried over magnesium sulfate, evaporated, and the residue is purified to give 5-(4-methylpiperazino)- imidazo[2,1-b][1,3,5]benzothiadiazepine melting at 145°–7° and identical to compound obtained in Example 1.

EXAMPLE 14

Preparation of 10,000 tablets each containing 5 mg of the active ingredient:

| Formula: | |
|---|---|
| 5-(4-methylpiperazino)-imidazo[2,1-b][1,3,5]benzothiadiazepine maleate | 50.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 15

Preparation of 10,000 capsules each containing 10 mg of the active ingredient:

| Formula: | |
|---|---|
| 5-[4-(2-hydroxyethyl)-piperazino]-imidazo[2,1-b][1,3,5]benzothiadiazepine dihydrochloride | 100.0 g |
| Lactose | 1,800.0 g |
| Talcum powder | 100.0 g |

Procedure:

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

Analogously tablets or capsules are prepared from the remaining compounds of the invention, e.g. those illustrated by the other examples herein.

What is claimed is:

1. A 5-diazacycloalkyl-imidazo[2,1-b][1,3,5]benzothiadiazepine compound of the formula

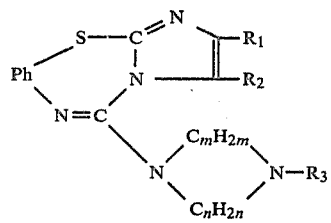

wherein each of $R_1$ and $R_2$ is hydrogen or lower alkyl; Ph is 1,2-phenylene, unsubstituted or substituted by one member selected from lower alkyl, lower alkoxy, lower alkylthio, halogeno, trifluoromethyl, sulfamoyl, mono- or di-lower alkylsulfamoyl; $C_mH_{2m}$ is lower alkylene separating both nitrogen atoms by 2 carbon atoms; $C_nH_{2n}$ is lower alkylene separating both nitrogen atoms by 3 carbon atoms; and $R_3$ is lower alkyl or lower hydroxyalkyl wherein the hydroxy group is separated from the nitrogen atom by 2 carbon atoms; the oxides thereof; or a pharmaceutically acceptable salt thereof.

2. A compound as claimed in claim 1, in which formula each of $R_1$ and $R_2$ is hydrogen or lower alkyl; Ph is 1,2-phenylene, (lower alkyl)-1,2-phenylene, (lower alkoxy)-1,2-phenylene, (lower alkylthio)-1,2-phenylene, (halogeno)-1,2-phenylene, (trifluoromethyl)-1,2-phenylene, (sulfamoyl)-1,2-phenylene, (mono- or di-lower alkylsulfamoyl)-1,2-phenylene; m is the integer 2; n is the integer 3; and $R_3$ is lower alkyl or lower hydroxyalkyl wherein the hydroxy group is separated from the nitrogen atom by 2 carbon atoms; the oxides thereof; or a pharmaceutically acceptable acid addition salt thereof.

3. A compound as claimed in claim 2 being 5-(4-methylhomopiperazino)imidazo[2,1-b][1,3,5]benzothiadiazepine or a pharmaceutically acceptable salt thereof.

* * * * *